(12) United States Patent
Lines et al.

(10) Patent No.: US 8,318,224 B2
(45) Date of Patent: Nov. 27, 2012

(54) COMPOSITION FOR ENHANCING PHYSICAL PERFORMANCE

(75) Inventors: Thomas Christian Lines, Hassel (LU); Mitsunori Ono, Lexington, MA (US)

(73) Assignee: The FRS Company, Foster City, CA (US)

(*) Notice: Subject to any disclaimer, the term of this patent is extended or adjusted under 35 U.S.C. 154(b) by 1213 days.

(21) Appl. No.: 11/675,576

(22) Filed: Feb. 15, 2007

(65) Prior Publication Data
US 2007/0148210 A1 Jun. 28, 2007

Related U.S. Application Data

(63) Continuation of application No. 10/692,178, filed on Oct. 23, 2003, now abandoned, and a continuation-in-part of application No. 10/302,544, filed on Nov. 22, 2002, now Pat. No. 6,821,536.

(60) Provisional application No. 60/420,986, filed on Oct. 23, 2002.

(51) Int. Cl.
*A23L 1/302* (2006.01)

(52) U.S. Cl. .............. 426/72; 426/2; 426/73; 426/541; 426/549; 426/590; 426/597

(58) Field of Classification Search .............. 514/457, 514/355, 474; 426/72, 73, 541, 549, 590, 426/597, 2
See application file for complete search history.

(56) References Cited

U.S. PATENT DOCUMENTS

| | | | |
|---|---|---|---|
| 5,026,721 | A | 6/1991 | Dudrick et al. |
| 5,846,569 | A | 12/1998 | Anderson et al. |
| 6,210,701 | B1 | 4/2001 | Darland et al. |
| 6,261,589 | B1 | 7/2001 | Pearson et al. |
| 6,277,426 | B1 | 8/2001 | Reust |
| 6,277,427 | B1 | 8/2001 | Husz |
| 6,299,925 | B1 | 10/2001 | Xiong et al. |
| 6,551,629 | B1 | 4/2003 | Gorsek |
| 6,579,544 | B1 * | 6/2003 | Rosenberg et al. .......... 424/736 |
| 6,821,536 | B2 | 11/2004 | Lines et al. |
| 2002/0025350 | A1 | 2/2002 | Siddiqui et al. |
| 2003/0054357 | A1 | 3/2003 | Young et al. |
| 2003/0068391 | A1 | 4/2003 | Harris et al. |
| 2003/0108624 | A1 * | 6/2003 | Kosbab .................... 424/729 |
| 2005/0031737 | A1 | 2/2005 | Lines et al. |

FOREIGN PATENT DOCUMENTS

| | | |
|---|---|---|
| CA | 2284290 | 9/1998 |
| CN | 1114207 A | 1/1996 |
| WO | WO 00/12085 | 3/2000 |
| WO | WO 02/07768 A1 | 1/2002 |

OTHER PUBLICATIONS

Biz Ed, 1996-2011 "Red Bull Energy Drink", TM " http://www.bized.co.uk/compfact/redbull/redbullindex.htm?page=12, p. 1, Jul. 17, 2011.*
Wikipedia, Jul. 17, 2011, Red Bull, TM, http://en.wikipedia.org/wiki/Red_Bull, pp. 1-8.*
Dequan et al., "Survey of Bioflavonoids", Food and Fermentation Industries, vol. 25 (16), 52-56, 1999. (Translation of English Abstract).
Chow et al., "Phase I Pharmacokinetic Study of Tea Polyphenols Following Single-dose Administration of Epigallocatechin Gallate and Polyphenon E1", Cancer Epidemiology, Biomarkers & Prevention 10:53-58, 2001, XP-002366662.
Koo et al., Pharmacological Effects of Green Tea on the Gastrointestinal System, European Journal of Pharmacology 500:177-185, 2004.
Bors et al., "Flavanoids and Polyphenols: Chemistry and Biology", *Handbook of Antioxidants*, pp. 409-416 (1996).
Crespy et al., "Quercetin, but not Its Glycosides, Is Absorbed from the Rat Stomach", *Journal of Agricultural and Food Chemistry*, vol. 50, pp. 68-621 (2002).
Erlund et al., "Pharmacokinetics of quercetin from quercetin aglycone and rutin in healthy volunteers", *Eur. J. Clin. Pharmacol*, vol. 56, pp. 545-553 (2000).
Guardia et al., "Anti-inflammatory properties of plant flavanoids. Effects of rutin, quercetin and hesperidin on adjuvant arthritis in rat", *Il Farmaco*, vol. 56, pp. 683-687 (2001).
Saucier et al., "Synergetic Activity of Catechin and Other Antioxidants", *Journal of Agricultural and Food Chemistry*, vol. 47, No. 11, pp. 44914494 (Nov. 1999).
Sesink et al., "Quercetin Glucuronides but Not Glucosides Are Present in Human Plasma after Consumption of Quercetin-3-Glucoside or Quercetin-4'-Glucoside $^I$ ", *Human Nutrition and Metabolism Research Communication*, pp. 1938-1941 (2001).
Thomas et al., "Ascorbate and Phenolic Antioxidant Interactions in Prevention of Liposomal Oxidation", *Lipids*, vol. 27, No. 7 (1992).
Walle et al., "Quercetin Glucosides Are Completely Hydrolyzed in Ileostomy Patients before Absorption", *Human Nutrition and Metabolism Research Communication*, pp. 2658-1661 (2000).
Hakkinen, et al. "Content of the Flavonols Quercetin, Myricetin, and Kaempferol in 25 Edible Berries", J. Agricultural Food Chem. Dec. 1999, vol. 47, pp. 2274-2279.
http://web.archive.org/web/20011202000359/www.oceanspray.com/cran_health.htm. Accessed Dec. 2, 2001.

(Continued)

*Primary Examiner* — Helen F Heggestad
(74) *Attorney, Agent, or Firm* — Knobbe, Martens, Olson & Bear, LLP

(57) ABSTRACT

This invention relates to a composition that contains quercetin, vitamin B1, vitamin B2, vitamin B3, vitamin B6, vitamin B12, vitamin C, caffeine, epigallocatechin gallate, epicatechin, epicatechin gallate, and epigallocatechin.

23 Claims, No Drawings

OTHER PUBLICATIONS

Min, et al., "The Chemistry and Medical Application of Tea Polyphenol", Hubei Chemical Industry, 2001, 3, 29-31. (Translation of English Abstract).

Yin et al., "The essential mechanisms of aging: Irreparable damage accumulation of biochemical side-reactions", Exp Gerontol. (2005) 40(6):455-465.

* cited by examiner

_(1)_

COMPOSITION FOR ENHANCING PHYSICAL PERFORMANCE

CROSS REFERENCE TO RELATED APPLICATION

This application is a continuation of U.S. application Ser. No. 10/692,178, filed Oct. 23, 2003, now abandoned which claims priority to U.S. application Ser. No. 60/420,986, filed Oct. 23, 2002, and is a continuation-in-part of U.S. application Ser. No. 10/302,544, filed Nov. 22, 2002, which matured into U.S. Pat. No. 6,821,536, issued Nov. 23, 2004. The contents of the prior applications are incorporated herein by reference.

BACKGROUND

Achieving peak physical performance has long been a goal for athletic competition and self-improvement. Means for improving physical performance includes prolonged systematic exercise, proper diet, and use of pharmaceuticals such as anabolic steroids. Anabolic steroids, which are testosterone derivatives, promote tissue growth, increase muscle mass, increase blood volume and hemoglobin level, and improve overall strength. Nonetheless, the use of anabolic steroids often results in serious complications, such as decreased blood high-density lipoprotein levels, disorders of the reproductive system, and disorders of the liver including carcinoma and peliosis hepatis. These complications further lead to virilization in females, interrupted growth in children, and defects in fetuses. The use of anabolic steroid can also cause psychological disorders such as unpredictable mood changes and aggression. Thus, there is a need for a safe drug or dietary supplement for enhancing physical performance.

SUMMARY

This invention relates to a composition that contains quercetin and a number of other natural products. The composition can be used in enhancing physical performance, i.e., improving an ability to perform an exercise, such as speed, strength, power, endurance, flexibility, agility, balance, focus coordination, reaction time, and fatigue recovery.

One aspect of this invention features a composition that contains quercetin and one or both of vitamin B3 and C. In one embodiment, the composition further contains at least one of the following ingredients: vitamin B1, vitamin B2, vitamin B6, and vitamin B12. In another embodiment, it further contains at least one of caffeine, epigallocatechin gallate, epicatechin, epicatechin gallate, epigallocatechin, and polypheron E. This composition may also contain other ingredients, such as vitamin E, CoQ-10, soy isoflavones, taurine, sugar beet pectin fiber, and a ginko biloba extract. Further, the composition can be sweetened, if necessary, by adding a sweetener, e.g., sorbitol, maltitol, cane sugar, high fructose corn syrup, and the like. The composition can also contain amino acids, minerals, a flavor enhancer, or a coloring agent. It is known that the leaves of green tea contain epigallocatechin gallate, epicatechin, epicatechin gallate, epigallocatechin, and polypheron E. Thus, these five ingredients can be conveniently provided as a green tea extract.

The composition of the invention can be in dry form (e.g., power or tablet) or in aqueous form (e.g., beverage or syrup). It can be a dietary supplement or a pharmaceutical formulation. It can also be a drink or a food product. Examples include tea (e.g., a tea drink and the contents of a tea bag), soft drinks, juice (e.g., a fruit extract and a juice drink), milk, coffee, jelly, ice cream, yogurt, cookies, cereals, chocolates, and snack bars. The composition, in any of the forms described above, can be used to enhance physical performance. Also within the scope of this invention is a composition of the invention as an active agent, as well as use of the composition for the manufacture of a medicament, for enhancing physical performance.

The invention also features a method for enhancing physical performance. The method includes administering to a subject in need thereof an effective amount of the above-described composition. By proper administrating the composition as detailed below, physical performance can be enhanced without the deleterious side effects of pharmaceutical performance enhancers, such as anabolic steroids.

The details of one or more embodiments of the invention are set forth in the accompanying description below. Other features, objects, and advantages of the invention will be apparent from the description and from the claims.

DETAILED DESCRIPTION

This invention is based, at least in part, on the unexpected discovery that quercetin, an antioxidant, and a number of other natural products exhibit synergistic health benefits, including enhancing physical performance in a subject.

For example, within the scope of this invention is a quercetin-containing composition that includes vitamin B3 or vitamin C, or both. It further contains one or more of vitamin B1, vitamin B2, vitamin B6, and vitamin B12. The composition can also contain one or more of caffeine, epigallocatechin gallate, epicatechin, epicatechin gallate, epigallocatechin, and polypheron E. A green tea extract can be conveniently used to provide epigallocatechin gallate, epicatechin, epicatechin gallate, epigallocatechin, and polypheron E.

Exemplary quantities of the ingredients of this composition are: 0.1-50 mg of vitamin B1, 0.1-150 mg of vitamin B2, 0.1-2000 mg of vitamin B3, 0.1-200 mg of vitamin B6, 5-150 μg of vitamin B12, 50-2000 mg of vitamin C, 50-1500 mg of caffeine, 20-2000 mg of quercetin, 10-500 mg of epigallocatechin gallate, 10-500 mg of epicatechin, 10-500 mg of epicatechin gallate, 10-500 mg of epigallocatechin, and 10-500 mg of polypheron E, which can be dissolved or dispersed in a 1 L aqueous solution. The quantities of the ingredients can also be those of the same relative ratio to those listed above. The term "quercetin" refers to both quercetin aglycon and quercetin derivatives, e.g., quercetin-3-O-glucoside, quercetin-5-O-glucoside, quercetin-7-O-glucoside, quercetin-9-O-glucoside, quercetin-3-O-rutinoside, quercetin-3-O-[α-rhamnosyl-(1→2)-α-rhamnosyl-(1→6)]-β-glucoside, quercetin-3-O-galactoside, quercetin-7-O-galactoside, quercetin-3-O-rhamnoside, and quercetin-7-O-galactoside. After digestion, quercetin derivatives are converted to quercetin aglycon, an active form absorbed in the body. The quantity of quercetin mentioned above refers to that of quercetin aglycon or the quercetin moiety of a quercetin derivative. As an example, a composition for daily used can be a 1 L aqueous solution containing 1000 mg of quercetin, 30 mg of vitamin B1, 85 mg of vitamin B2, 1 g of vitamin B3, 100 mg of vitamin B6, 120 μg of vitamin B12, 1200 mg of vitamin C, 1000 IU of vitamin E, 1000 mg of caffeine, and a green tea extract containing 120 mg of epigallocatechin gallate, 140 mg of epicatechin, 360 mg of epicatechin gallate, 360 mg of epigallocatechin, and 120 mg of polypheron E.

This composition may also contain one or more other active ingredients, such as vitamin E, CoQ-10, soy isoflavones, taurine, sugar beet pectin fiber, and a ginko biloba extract. Exemplary quantities of these ingredients are: 3-1000 IU of vitamin E, 10-400 mg of CoQ-10, 20-600 mg of soy isoflavones, 10-1000 mg of taurine, 1-15 g of sugar beet pectin fiber, and 50-500 mg of a ginko biloba extract (dry weight). Further, the composition can be sweetened, if necessary, by adding a sweetener such as sorbitol, maltitol, hydrogenated glucose syrup and hydrogenated starch hydrolyzate, high fructose corn syrup, cane sugar, beet sugar, pectin, and sucralose.

An example of the above-describes composition is a powder. It can be used conveniently to prepare beverages, e.g., tea or juice. The powder can also be used to prepare paste, jelly, capsules, or tablets. Lactose and corn starch are commonly used as diluents for capsules and as carriers for tablets. Lubricating agents, such as magnesium stearate, are typically added to form tablets.

The composition of the invention can also be a dietary supplement or a pharmaceutical formulation. As a dietary supplement, additional nutrients, such as minerals or amino acids may be included. The composition can also be a drink or food product. As used herein, the terms "drink" and "food" broadly refer to any kinds of liquid and solid/semi-solid materials, respectively, that are used for nourishing an animal, and for sustaining normal or accelerated growth of an animal including a human. Examples of the drink product include, but are not limited to, tea-based beverages, juice, coffee, and milk. Examples of the food product include jelly, cookies, cereals, chocolates, snack bars, herbal extracts, dairy products (e.g., ice cream, and yogurt), soy bean product (e.g., tofu), and rice products.

The above-described composition, in any of the forms described above, can be used for enhancing physical performance. As shown in the examples below, the composition improves overall strength, balance, fatigue recovery, intensity of physical exercise, and endurance to the exercise. It can also be used for treating diseases or disorders, such as arthritis, tumor, diabetes, sexual dysfunction, chronic constipation, inflammatory bowel disease; improving concentration or mood; and lowering cholesterol levels of blood pressure. A "tumor" refers to benign tumor, as well as malignant tumor (e.g., leukemia, colon cancer, kidney cancer, liver cancer, breast cancer, or lung cancer).

The terms "improving", "treating," and "lowering" refer to the administration of an effective amount of a composition of the invention to a subject, who needs to improve his physical performance or has one or more of the just-mentioned disorders, or symptom or a predisposition of one of more of the disorders, with the purpose to improve physical performance or to cure, alleviate, relieve, remedy, or ameliorate one or more of the disorders, or the symptoms or the predispositions of one or more of them. The term "administtration" covers oral or parenteral delivery to a subject a composition of the invention in any suitable form, e.g., food product, beverage, tablet, capsule, suspension, and solution. The term "parenteral" refers to subcutaneous, intracutaneous, intravenous, intramuscular, intraarticular, intraarterial, intrasynovial, intrasternal, intrathecal, intralesional, and intracranial injection, as well as various infusion techniques. An "effective amount" refers to a dose of the composition that is sufficient to provide a physical benefit (e.g., improving endurance) or a therapeutic benefit (e.g., lowering cholesterol levels or blood pressure). Both in vivo and in vitro studies can be conducted to determine optimal administration routes and doses.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

Composition A (1000 ml) was prepared by mixing the following ingredients at room temperature: 1000 ml of orange juice, 1000 mg of quercetin, 30 mg of vitamin B1, 85 mg of vitamin B2, 1000 mg of vitamin B3, 100 mg of vitamin B6, 120 αg of vitamin B12, 1000 IU of vitamin E, and 1000 mg of caffeine. All ingredients were obtained from Spectrum Laboratory products, Inc., Gardena, Calif.; Sigma, St. Louis, Mo.; and Aldrich, Milwaukee, Wis.

Ten male Spregue-Dawley rats, weighing 240-250 g, were obtained from Charles River Lab (Boston, Mass.). The rats were divided into Groups 1 and 2 (5 in each group). The rats in the Group 2 were administered by intragastric feeding with the just-described composition at a daily dose of 8 ml/rat (30 ml/kg body weight) for 48 days. The rats in Group 1 were administered with water.

At days 0, 14, 28, and 42 after the administration, blood samples were collected from the rats by supraorbital bleeding and various hematological parameters were determine using standard methods. The results are summarized in Tables 1 and 2 below.

TABLE 1

Effects of composition A on rat hemotological parameters

| Parameter | Reference Range | Day 0 | | Day 14 | | Day 28 | | Day 42 | |
|---|---|---|---|---|---|---|---|---|---|
| | | Group 1 | Group 2 | Group 1 | Group 2 | Group 1 | Group 2 | Group 1 | Group 2 |
| WBC | 9.4-14.9 (THSN/UL) | 17.22 | 15.04 | 17.34 | 16.50 | 18.76 | 16.90 | 17.66 | 14.20 |
| RBC | 6.2-9.0 (MILL/UL) | 6.09 | 5.94 | 6.63 | 6.60 | 7.43 | 7.20 | 7.99 | 7.72 |
| Hb | 13.4-16.4 (GM/DL) | 12.46 | 12.38 | 14.24 | 14.40 | 15.32 | 15.02 | 15.86 | 15.18 |
| Hematocrit | 40.0-49.0 (%) | 37.80 | 37.44 | 42.30 | 43.26 | 45.56 | 45.00 | 47.04 | 45.86 |
| MCV | 52.0-66.0 (FL) | 62.20 | 63.20 | 63.80 | 65.40 | 61.60 | 62.60 | 58.80 | 59.40 |
| MCH | 17.7-19.1 (PICO GM) | 20.46 | 20.84 | 21.50 | 21.82 | 20.68 | 20.86 | 19.88 | 19.72 |
| MCHC | 32.0-33.5 (%) | 32.96 | 33.00 | 33.64 | 33.26 | 33.66 | 33.38 | 33.72 | 33.14 |
| Platelet | 780-1400 (THSN/UL) | 956.00 | 965.00 | 1084.60 | 1158.80 | 1078.40 | 1076.60 | 967.00 | 962.80 |
| BANDS | 0.00-0.06 | 0.00 | 0.00 | 0.00 | 0.00 | 0.00 | 0.00 | 0.00 | 0.00 |

TABLE 1-continued

Effects of composition A on rat hemotological parameters

| Parameter | Reference Range | Day 0 Group 1 | Day 0 Group 2 | Day 14 Group 1 | Day 14 Group 2 | Day 28 Group 1 | Day 28 Group 2 | Day 42 Group 1 | Day 42 Group 2 |
|---|---|---|---|---|---|---|---|---|---|
| Segmented Nestrophiles | 0.58-6.30 (THSN/UL) | 4.44 | 4.78 | 3.34 | 3.59 | 3.41 | 3.33 | 3.27 | 3.60 |
| Lymphocyte | 3.78-14.9 (THSN/UL) | 10.07 | 7.84 | 12.10 | 11.02 | 13.52 | 11.99 | 12.78 | 9.37 |
| Monocyte | 0.02-1.20 (THSN/UL) | 3.43 | 2.15 | 1.67 | 1.67 | 1.49 | 1.30 | 1.24 | 1.03 |
| Eosinophiles | 0.00-0.01 (THSN/UL) | 0.54 | 0.16 | 0.11 | 0.10 | 0.17 | 0.13 | 0.20 | 0.10 |
| Basophiles | 0.00-0.00 (THSN/UL) | 0.14 | 0.11 | 0.12 | 0.12 | 0.17 | 0.15 | 0.16 | 0.09 |
| Atipicle Lymphocyte | 0.00-0.00 (THSN/UL) | 0.02 | 0.00 | 0.00 | 0.00 | 0.00 | 0.00 | 0.00 | 0.00 |
| Metamyelocytes | 0.00-0.00 (THSN/UL) | 0.00 | 0.00 | 0.00 | 0.00 | 0.00 | 0.00 | 0.00 | 0.00 |
| Myelocytes | 0.00-0.00 (THSN/UL) | 0.00 | 0.00 | 0.00 | 0.00 | 0.00 | 0.00 | 0.00 | 0.00 |
| NRBC/100WBC | 0-0 (/100WBC) | 0.60 | 0.40 | 0.00 | 0.00 | 0.00 | 0.00 | 0.00 | 0.00 |
| Reticulocyte | 0.1-4.0 (%) | 1 | 1 | 2.62 | 5.74 | 3.30 | 5.90 | 4.78 | 6.58 |

Note:
WBC: white blood cell
RBC: red blood cell
Hb: hemoglobin
MCV: mean corpuscular volume
MCH: hemoglobin amount per red blood cell
MCHC: mean cell hemoglobin concentration
BANDS: premature neutrophil
NRBC: nucleated red blood cell count
THSN/UL: 1,000/ul
MILL/UL: 1,000,000/ul
GM/DL: gram/dl
FL: femtoliter
PICO GM: picogram

TABLE 2

Effects of composition A on rat reticulocyte level

| Group | Ref. Range (%) | Day | 1# | 2# | 3# | 4# | 5# | Average | SD |
|---|---|---|---|---|---|---|---|---|---|
| 1 | 0.1-4.0 | 14 | 2.9 | 2.9 | 2 | 4.9 | 4.4 | 2.62 | 0.96 |
| 2 | 0.1-4.0 | 14 | 5.8 | 4.9 | 7.5 | 5.8 | 4.7 | 5.74 | 2.15 |
| 1 | 0.1-4.0 | 28 | 3.1 | 2.2 | 2.2 | 7.2 | 6.8 | 3.30 | 2.5 |
| 2 | 0.1-4.0 | 28 | 4.8 | 6.5 | 5.4 | 5.5 | 7.3 | 5.90 | 1.3 |
| 1 | 0.1-4.0 | 42 | 4.8 | 9.2 | 9 | 5.5 | 5.4 | 4.78 | 2.14 |
| 2 | 0.1-4.0 | 42 | 7.5 | 6.2 | 6.1 | 6.4 | 6.7 | 6.58 | 0.16 |

Note:
SD = Standard Deviation

As shown in Tables 1 and 2, the reticulocyte levels in the rats administered with composition B (Group 2) were higher than those in the rats administered with water (Group 1). For example, at Day 42, the average reticulocyte level in the rats of Group 2 (6.58%) was higher than that in the rats of Group 1 (4.78%) by 37.7%. On the other hand, other hematological parameters of the rats in the two groups did not differ significantly. See Table 1. The results indicate that composition A increases the reticulocyte level but does not affect other hematological parameters. Reticulocytes are immature, anucleated red blood cells (RBCs). An increase in the reticulocyte level and no changes in other hematological parameters suggest that composition A improves the renewal of RBC.

During the experiment, the body weight of each rat was monitored daily. No statistical difference was found between the two groups.

EXAMPLE 2

Composition B (1000 ml) was prepared by mixing the following ingredients at room temperature: 1000 ml of orange juice, 1000 mg of quercetin, 30 mg of vitamin B1, 85 mg of vitamin B2, 1000 mg of B3, 100 mg of vitamin B6, 120 µg of vitamin B12, 1000 IU of vitamin E, 1000 mg of caffeine, 500 mg of epigallocatechin gallate, 500 mg of epicatechin, 500 mg of epicateqin gallate, 500 mg of epigallocatechin, and 500 mg of polypheron E.

Ten male Spregue-Dawley rats that weighted 240-250 g were divided into Groups 1 and 2 (5 in each group). The rats in Group 2 were administered by intragastric feeding with composition B at an average daily dose of 14 ml/kg body weight for 95 days. Those in Group 1 were administered with water.

Starting form Day 92 after the administration, each of the rats was trained on a Rota-Rod treadmill (Model 57750, Stoelting Co., Wood Dale, Ill.) for over 2 hours. At Day 95, after being trained for another 20 minutes, each of the rats was put on the treadmill and allowed to walk. The time for which each rat walked on the treadmill before falling off was recorded and the average time for the rats in Groups 1 and 2 determined. The experiments were repeated for three times ("Test A," "Test B," and "Test C"). The results are summarize in Table 3 below.

TABLE 3

Effects of composition B

| Groups | Time on Rota-Rod treadmill (min) | | |
|---|---|---|---|
| | Test A | Test B | Test C |
| Group 1 | | | |
| #1 | 2.36 | 13.11 | 23.33 |
| #2 | 10.69 | 16.02 | 44.21 |
| #3 | 19.02 | 15.46 | 66.90 |
| #4 | 2.99 | 16.67 | 16.09 |
| #5 | 1.34 | 3.41 | 7.82 |
| Average | 7.28 | 12.93 | 31.67 |
| SE | 3.37 | 2.45 | 10.68 |
| Group 2 | | | |
| #1 | 6.54 | 61.95 | 80.40 |
| #2 | 16.16 | 21.54 | 41.73 |
| #3 | 6.91 | 23.83 | 90.47 |
| #4 | 24.19 | 20.42 | 202.82 |
| #5 | 32.58 | 15.37 | 67.44 |
| Average | 17.28 | 28.62 | 96.57 |
| SE | 5.03 | 8.45 | 27.79 |

Note:
SE = Standard Error

As shown in Table 3, the rats got used to the exercise and walked for longer time on the treadmill as the experiment went on. In all tests, the rats that had been administered with composition B walked on the treadmill longer than those that had been not. These results indicate that composition B enhanced the physical performance of rats. During the 95 days of administration, the body weight of each rat was monitored daily. No statistical difference was found between Groups 1 and 2. This result suggests the enhanced physical performance of the rats in Group 2 was not due to an increase in body mass.

OTHER EMBODIMENTS

All of the features disclosed in this specification may be combined in any combination. Each feature disclosed in this specification may be replaces by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method for improving overall strength in a mammal in need of or desiring an improvement in overall strength, comprising:
    administering a preparation comprising 20-2000 mg quercetin, 50-2000 mg vitamin C, and 0.1-2000 mg vitamin B3 to the mammal, thereby resulting in said mammal having improved overall strength wherein the preparation comprises a composition selected from the group consisting of a liquid supplement, a tablet, and a powder.

2. The method of claim 1, wherein the preparation further comprises a green tea extract containing at least one of caffeine, epigallocatechin gallate, epicatechin, epicatechin gallate, epigallocatechin, and polypheron E.

3. The method of claim 1, wherein the preparation comprises approximately equal parts of quercetin and B3.

4. The method of claim 1, wherein the mammal is a human.

5. A method according to claim 1, wherein the preparation consists essentially of quercetin, vitamin C, and vitamin B3.

6. A method according to claim 1, wherein the mammal is also in need of or desiring of an increase in fatigue recovery in the mammal.

7. A method according to claim 1, wherein the mammal is also in need of or desiring of an increase in endurance.

8. A method for increasing fatigue recovery in a mammal in need of or desiring an increase in fatigue recovery, comprising:
    administering a preparation comprising 20-2000 mg quercetin, 50-2000 mg vitamin C, and 0.1-2000 mg vitamin B3 to the mammal, thereby resulting in said mammal having increased skeletal muscle mass, wherein the preparation comprises a composition selected from the group consisting of a liquid supplement, a tablet, and a powder.

9. The method of claim 8, wherein the preparation comprises approximately equal parts of quercetin and B3.

10. The method of claim 8, wherein the mammal is a human.

11. A method according to claim 8, wherein the preparation consists essentially of quercetin, vitamin C, and vitamin B3.

12. A method according to claim 8, wherein the mammal is also in need of or desiring of an increase in endurance.

13. The method of claim 8, wherein the preparation further comprises a green tea extract comprising at least one of caffeine, epigallocatechin gallate, epicatechin, epicatechin gallate, epigallocatechin, and polypheron E.

14. The method of claim 1, further comprising at least one of vitamin B1, vitamin B2, vitamin B6, vitamin B12, and vitamin E.

15. The method of claims 1, further comprising at least one of CoQ-10, soy isoflavones, sugar beet pectin fiber, and a ginko biloba extract.

16. The method of claims 1, further comprising taurine.

17. The method of claim 16, wherein the taurine is present in an amount of 10-1000 mg.

18. A method for increasing endurance in a mammal in need of or desiring an increase in endurance, comprising:
    administering a preparation comprising 20-2000 mg quercetin, 50-2000 mg vitamin C, and 0.1-2000 mg vitamin B3 to the mammal, thereby resulting in said mammal having increased endurance, wherein the preparation comprises a composition selected from the group consisting of a liquid supplement, a tablet, and a powder.

19. The method of claim 18, wherein the preparation further comprises a green tea extract comprising at least one of caffeine, epigallocatechin gallate, epicatechin, epicatechin gallate, epigallocatechin, and polypheron E.

20. The method of claim 18, wherein the preparation comprises approximately equal parts of quercetin and B3.

21. The method of claim 18, wherein the mammal is a human.

22. A method according to claim 18, wherein the preparation consists essentially of quercetin, vitamin C, and vitamin B3.

23. A method according to claim 18, wherein the mammal is also in need of or desiring of an increase in skeletal muscle mass and an improvement in overall strength.

* * * * *

UNITED STATES PATENT AND TRADEMARK OFFICE
CERTIFICATE OF CORRECTION

| | |
|---|---|
| PATENT NO. | : 8,318,224 B2 |
| APPLICATION NO. | : 11/675576 |
| DATED | : November 27, 2012 |
| INVENTOR(S) | : Thomas Christian Lines et al. |

It is certified that error appears in the above-identified patent and that said Letters Patent is hereby corrected as shown below:

Title Page, Line 17, Under Other Publications, change ""Flavanoids" to --"Flavonoids--.

Title Page, Line 25, Under Other Publications, change "flavanoids." to --flavonoids.--.

Title Page, Line 27, Under Other Publications, change "I1" to --Il--.

Title Page, Line 40, Under Other Publications, change "Flavonols" to --Flavonoids--.

In the Specifications

Column 1, Line 53, Change "ginko" to --ginkgo--.

Column 1, Line 63, Change "power" to --powder--.

Column 2, Line 57, Change "used" to --use--.

Column 2, Line 67, Change "ginko" to --ginkgo--.

Column 3, Line 4, Change "ginko" to --ginkgo--.

Column 3, Line 10, Change "describes" to --described--.

Column 3, Line 17, Change "the" to --this--.

Column 3, Line 39, Change "of" to --or--.

Column 3, Line 47, Change "symptom" to --a symptom--.

Column 4, Line 4, Change ""administtration"" to --"administration"--.

Column 4, Line 33, Change "120 $\alpha$g" to --120 μg--.

Column 4, Line 35, Change "products," to --Products,--.

Column 4, Line 46, Change "determine" to --determined--.

Column 4, Line 50, Change "hemotological" to --hematological--.

Column 4, Line 51, Change "Day14" to --Day 14--.

Column 5, Line 2, Change "hemotological" to --hematological--.

Column 5, Line 3, Change "Day14" to --Day 14--.

Column 5, Line 7, Change "Nestrophiles" to --Neutrophils--.

Signed and Sealed this
Fourth Day of June, 2013

Teresa Stanek Rea
*Acting Director of the United States Patent and Trademark Office*

CERTIFICATE OF CORRECTION (continued)
U.S. Pat. No. 8,318,224 B2

Column 5, Line 16, Change "Atipicle" to --Atypical--.

Column 5, Line 61, Change "The" to --These--.

Column 6, Line 47, Change "B3," to --vitamin B3,--.

Column 6, Line 50, Change "epicateqin" to --epicatechin--.

Column 6, Line 52, Change "weighted" to --weighed--.

Column 6, Line 58, Change "form" to --from--.

Column 6, Line 66, Change "summarize" to --summarized--.

Column 7, Line 42, Change "replaces" to --replaced--.

In the Claims

Column 8, Line 36, In Claim 15, change "claims" to --claim--.

Column 8, Line 38, In Claim 15, change "ginko" to --ginkgo--.

Column 8, Line 39, In Claim 16, change "claims" to --claim--.